United States Patent [19]

Shaw et al.

[11] 4,318,904

[45] Mar. 9, 1982

[54] PEPTIDE AFFINITY LABELS FOR THROMBIN AND OTHER TRYPSIN-LIKE PROTEASES

[75] Inventors: Elliott N. Shaw, Shoreham; Charles A. Kettner, Yaphank, both of N.Y.

[73] Assignee: Research Corporation, New York, N.Y.

[21] Appl. No.: 143,897

[22] Filed: Apr. 25, 1980

[51] Int. Cl.³ .................. A61K 37/00; C07D 237/00; C07D 00/00; C07C 103/52
[52] U.S. Cl. .................................. 424/177; 546/231; 260/112.5 R; 260/239 A
[58] Field of Search ............... 546/231; 260/239 AR, 260/112.5 R; 424/177

[56] References Cited

U.S. PATENT DOCUMENTS 3,884,896  5/1975  Blomback et al. ........... 260/112.5 R
4,061,625  12/1977  Ekenstam et al. ........... 260/112.5 R

OTHER PUBLICATIONS

Kirby, et al., Biochemistry, vol. 18, pp. 3564–3570 (1979).
Kettner & Shaw in "Chemistry and Biology of Thrombin", edited by Lundblad, Fenton/Mann, 1977, 129–143.
Kettner/Shaw, Biochemistry 17, 4778–4784 (1978).
Bajusz, et al., Peptides: Chemistry, Structure, Biology, 603–608, 1975.

*Primary Examiner*—Delbert R. Phillips

*Attorney, Agent, or Firm*—Oblon, Fisher, Spivak, McClelland & Maier

[57] ABSTRACT

A peptide affinity label of the formula (I):

$$Y-(D-)-NH-CH(Ar)-CO-N(CH_2\ J)-CH-CONH-CH((CH_2)_3-NH-C(=NH)NH_2)-C(=O)-CH(B)-X$$

wherein
 X is a radical capable of acting as a leaving group in a nucleophilic substitution reaction;
 A is an aromatic amino acid residue;
 B is H, or a $C_1$–$C_4$ alkyl group, or aryl;
 Y is selected from the group consisting of hydrogen, aroyl, $C_1$–$C_6$ acyl, and Q—(A)—$_n$, wherein
 Q=hydrogen, aroyl, or $C_1$–$C_6$ acyl,
 n=1-10,
 A is an amino acid residue selected from the aliphatic, hydroxy-containing, carboxylic acid group, and amide-thereof-containing, aromatic, sulfur-containing and imino-containing amino acids; and wherein
 J is selected from the group consisting of —$CH_2$—, —$CH_2$—$CH_2$—, —$CH_2$—$CH_2$—$CH_2$—, —CH=CH— and —CH(OH)—$CH_2$. The affinity label is useful for irreversibly inactivating thrombin and trypsin-like enzymes and may be used as a potential anticlotting agent.

12 Claims, 2 Drawing Figures

PEPTIDE AFFINITY LABELS FOR THROMBIN AND OTHER TRYPSIN-LIKE PROTEASES

BACKGROUND OF THE INVENTION

The U.S. Government has rights in this invention pursuant to Contract No. DE-AC02-76CH00016 between the U.S. Department of Energy and Associated Universities Inc.

1. Field of the Invention

The present invention relates to peptide-affinity labels (irreversible inhibitors) for thrombin-like proteases.

2. Description of the Prior Art

Thrombin and other trypsin-like proteases, such as plasminogen activators, are enzymes involved in the biochemical degradation of other polypeptides. They are characterized by having at the active site a reactive serine residue and a binding pocket having affinity for arginyl and lysyl residues.

Thrombin is an important endopeptidase involved in blood clotting in animals. Formation of a blood clot involves the transformation of a soluble plasma protein, fibrinogen, to an insoluble protein, fibrin. This transformation is enzymatically catalyzed by thrombin. Thrombin itself is generated from a pro-enzyme, prothrombin, by the enzymatic action of another proteolytic enzyme, factor Xa, which is in turn derived from a precursor, factor X, and so on. There are known to be 8 such proenzyme to enzyme transformations in blood clotting involving 8 factors respectively of which fibrinogen, prothrombin and factor X are but 3. The inhibition or inactivation of thrombin, the last factor in the cascade leading to blood clotting, would therefore constitute an effective control of blood clotting. If thrombin is inactivated, the transformation of fibrinogen to fibrin will not occur and blood coagulation will be prevented. The inhibition of thrombin has therefore been an active field of research.

Two types of inhibitors for proteolytic enzymes of the thrombin-type are, in principle, available. The *reversible* inhibitors are those that competitively or non-competitively bind to the enzyme in an association-dissociation equilibrium step (Equation 1):

$$\text{Enzyme} + \text{Inhibitor} \underset{}{\overset{K_i}{\rightleftharpoons}} [E \cdot I] \quad (1)$$
$$(E) \quad (I)$$

The dissociation constant $K_i$ is defined as the ratio of the rates of association ($k_{assoc}$) and dissociation ($k_{diss}$) (Equation 2):

$$K_i = \frac{k_{diss}}{k_{assoc}} \quad (2)$$

This definition of $K_i$ implies that inhibitors with large rates of association and small rates of dissociation ("good" inhibitors) will show small values of $K_i$.

Among the most effective reversible inhibitors of thrombin are those prepared by Bajusz et al (Peptides: Chemistry, Structure, Biology, Walter et al, eds., Ann Arbor, Mich., Ann Arbor Science Publishers, 1975, pp. 603–608). These authors prepared tripeptide aldehydes such as D-Ala-Pro-Arg-H D-Val-Pro-Arg-H or D-Phe-Pro-Arg-H. In these formulas, Ala stands for alanine, Pro stand for proline, Val stands for valine, Phe stands for phenyl alanine and Arg-H stands for the arginine aldehyde of the formula 3:

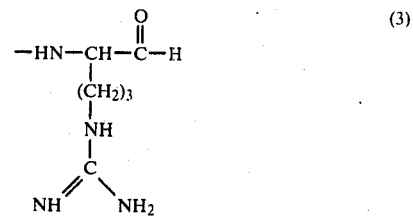

The use of the D-amino acid at the third or $P_3$ position increased the binding capacity of the overall tripeptide.

A second type of inhibitors for thrombin and trypsin-like enzymes are the so-called affinity labels. These inhibitors are *irreversible* inhibitors. The inhibitor carries in its structure a highly reactive, usually electrophilic, functionality such as a halomethyl ketone. The remainder of the affinity label is normally chosen so that it will show affinity for the active site of the enzyme in question and will enter into a preliminary, reversible binding step to form an enzyme-inhibitor complex. A reactive group at the active site of the enzyme, usually a nucleophile, then enters into a reaction with the electrophilic group of the label and is therefore "tagged" thereby. This sequence of steps is shown in Equation 4:

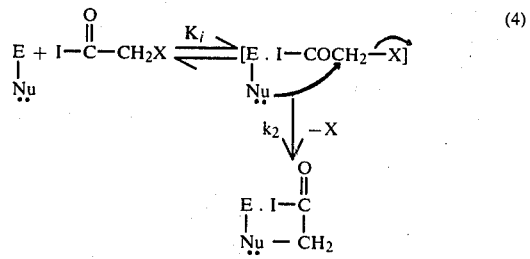

In this equation, Nü is a generalized nucleophile, such as for example, the imidazole nitrogen of a histidine side chain, X represents a halogen or other similar leaving group, I, E and $K_i$ are as defined previously. $k_2$ is the first order rate of covalent irreversible reaction of the active site nucleophile with the affinity label. Since reaction occurs at the enzyme active site, the enzyme is permanently blocked or inactivated.

A number of peptide affinity labels for thrombin have been reported; see for example, Kettner and Shaw, Chemistry and Biology of Thrombin, Lundblad et al, editors, Ann Arbor Science, pp. 129–143 (1977). The affinity labels described therein were generally selected from those having the sequence of the cleavage site of normal physiological substrates for thrombin. These physiological substrates include fibrinogen (A-chain), bovine prothrombin and human factor XIII.

Since thrombin and other trypsin-like serine proteases such as plasminogen activators (e.g., urokinase) are of critical importance in human physiology, a need continues to exist for highly selective affinity labels for these enzymes.

SUMMARY OF THE INVENTION

It is therefore an object of the invention to provide a selective affinity label for thrombin, thus providing a reagent which is an anticoagulant.

Another object of the invention is to provide a highly effective affinity labels for other trypsin-like proteases.

A still further object of the invention is to provide a potential tumor growth inhibitor.

These and other objects of the invention, which will hereinafter become readily more apparent, have been attained by providing a peptide affinity label of the formula (5):

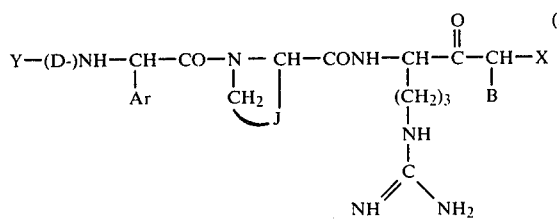

wherein:
X is a radical capable of acting as a leaving group in a nucleophilic substitution reaction;
B is —H, or —CH$_3$ or any other lower alky or aryl substituent;
Ar is an aromatic amino acid residue;
Y is selected from the group consisting of hydrogen, aroyl, C$_1$-C$_6$ acyl, and Q—(A)—$_n$ wherein Q=hydrogen, aroyl, or C$_1$-C$_6$ acyl;
n=1–10;
A is an amino acid residue preferably selected from the group consisting of the aliphatic, hydroxy-containing, carboxylic acid group- and amide thereof containing, basic, aromatic, sulfur-containing and imino-containing amino acids; and
where J is selected from the group consisting of —CH$_2$—CH$_2$—, —CH=CH—, —CH$_2$—CH$_2$—CH$_2$—, —CH(OH)—CH$_2$—, and —CH$_2$—.

Another object of the invention has been attained by providing pharmacological compositions comprising the peptides of formula (5) in combination with a pharmacologically inert carrier.

BRIEF DESCRIPTION OF THE DRAWINGS

A more complete appreciation of the invention and many of the attendant advantages thereof will be readily obtained as the same becomes better understood by reference to the following detailed description when considered in connection with the accompanying drawings, wherein.

DETAILED DESCRIPTION OF THE PREFERRED EMBODIMENTS

Figure 2:
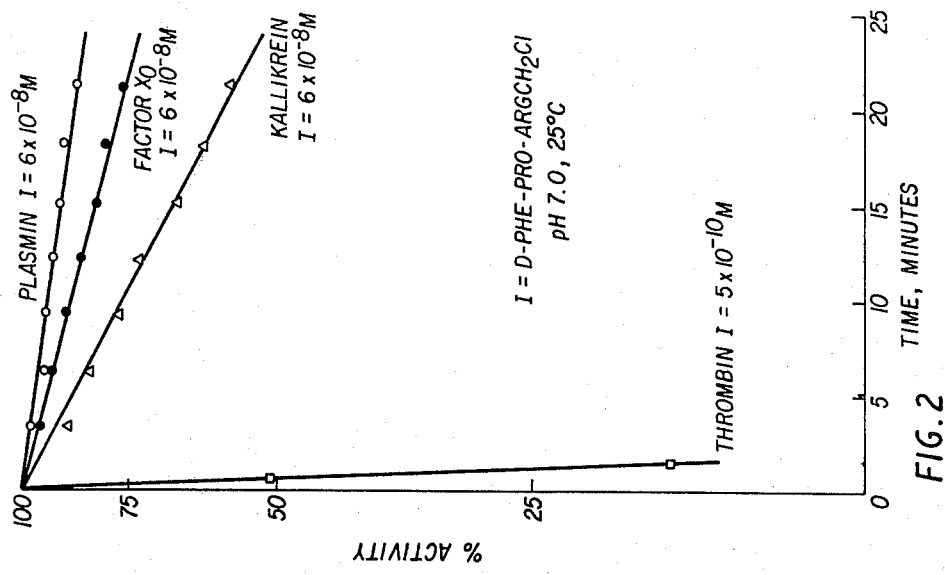
FIG. 2 shows the selectivity of D-Phe-Pro-Arg-CH$_2$Cl in the inactivation of thrombin when compared with other serine proteases, according to Example 3.

The essence of the present invention lies in the discovery that when X-methyl ketone-containing peptide affinity labels for thrombin-like enzymes are replaced at the third position thereof (position P$_3$) with a D-aromatic amino residue, a high degree of selectivity of the resulting affinity label for thrombin is obtained. The presence of a D-aromatic amino acid at the P$_3$ position is essential.

The affinity labels are those of formula (5) above. In this formula, X is a radical capable of acting as a leaving group in a nucleophilic substitution reaction, preferably X is a halogen atom, preferably chlorine, bromine, or iodine, most preferably chlorine; or another group such as tosyl, mesyl and the like. Ar is the residue of an aromatic amino acid such as for example, the residue of histidine (His), phenylalanine (Phe), C$_1$-C$_4$ alkyl substituted phenylalanine, tyrosine (Tyr), halo-substituted phenylalanine, such as iodo-substituted phenylalanine, tryptophan (trp) or thyroxine. Preferably, Ar is the residue of phenylalanine or tyrosine, most preferably, phenylalanine. J may form a single or double bond to complete a prolyl or dehydroprolyl residue at the P$_2$ position of the peptide. J may also be —CH(OH)—CH$_2$— or —CH$_2$—CH$_2$—CH$_2$—, or —CH$_2$— thereby forming a hydroxy prolyl, pipecolyl, or azetidinecarboxylate residue at P$_2$. B is hydrogen, lower alkyl such as C$_1$-C$_4$ alkyl or aryl, such as phenyl, tolyl, xylyl, napthyl and the like.

Y is an atom or radical bonded to the nitrogen atom of the D-residue of position P$_3$. Y may be hydrogen, aroyl such as benzoyl, C$_1$-C$_6$ acyl, such as acetyl or propionyl. In these cases, the peptide affinity label is a terminally N-acylated or non-acylated tripeptide affinity label. Y, on the other hand, may also be an amino acid or a polypeptidyl residue itself. The single amino acid or multiple amino acid residues forming such a polypeptidyl residue are selected from the group consisting of aliphatic amino acids, hydroxy-containing amino acids, carboxylic acid group-containing amino acids, their amides, basic amino acids, aromatic amino acids, sulfur-containing amino acids and cyclic amino acids (see, for example, Mahler and Cordes, Biological Chemistry, second edition, pp. 44–47, which is herein incorporated by reference). The aliphatic amino acids include glycine (gly), alanine (ala), valine (val), leucine (leu), and isoleucine (ile). The hydroxy amino acids include serine (ser), threonine (thr). The carboxylic amino acids include aspartic acid (asp), glutamic acid (glu) and their amides, asparagine (asn) and glutamine (gln). The basic amino acids include lysine (lys), hydroxy lysine (hydrlys), histidine (his) and arginine (arg). The aromatic amino acids include phenylalanine (phe), tyrosine (tyr), tryptophan (trp) and thyroxine (thyr). The sulfur-containing amino acids include cysteine, cystine and methionine (met). The cyclic amino acids include proline (pro) and hydroxy proline (hydrpro). When Y is a polypeptidyl residue, it is preferred that the primary sequence thereof correspond to the primary sequence of the enzymatic substrates themselves. This assures a potentially greater affinity of the polypeptide affinity label towards the enzyme active site. The relevant sequence of amino acids is that corresponding to the fourth (P$_4$), fifth (P$_5$), sixth (P$_6$), etc. residues of the substrates, towards the amino terminal, counting away from the residue P$_1$ at which cleavage occurs. The amino acid at the site of cleavage is counted as the first position. The A-chain of human fibrinogen for example, which is a physiological substrate of thrombin shows the following sequence starting at the cleavage residue Arg (position P$_1$) and counting towards the amino terminal (Blombäck, B. And Blombäck, M. (1972), *Ann. N.Y. Acad. Sci.* 202, 77–97; BlombULM/a/ck, B., Hessel, B., Iwanaga, S., Reuterby, J. and Blombäck, M., (1972) J. Biol. Chem., 247, 1496-1512):

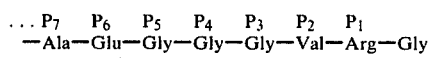
(6)

The corresponding sequences for the B-chain of human fibrinogen, prothrombin and factor XIII are also given below (Equations 7) (Blomback, B., and Blomback, M., (1972), Ann. N.Y. Acad. Sci. 202, 77-97; Magnusson, M., Petersen, T. E., Sottrup-Jensen, L., Claeys, H., (1975), in: Proteases and Biological Control (E. Reich, D. B. Rifkin and E. Shaw, eds.), Cold Spring Harbor Press, Cold Spring Harbor, N.Y., pp. 123-149; Takagi, T. and Doolittle, R. F. (1974), Biochemistry, 13, 750-756):

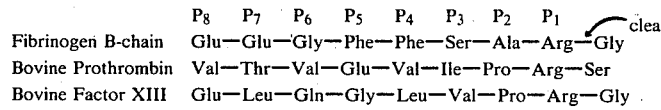

By choosing the appropriate amino acid residues $P_4$-$P_{14}$ so that they correspond to the natural substrates of the enzymes being inactivated and using as the $P_3$-$P_2$-$P_1$ residues those of the present invention, polypeptide affinity labels of varying degrees of affinity can be readily obtained. The most preferred peptide affinity labels are the tripeptide labels themselves, wherein Y represents hydrogen or an acyl or aroyl group. Most preferred are the tripeptides wherein Y represents hydrogen.

The amino acid residue at position $P_2$ is a cyclic amino or a proline derivative such as dehydroproline or 3-hydroxyproline. Preferred among these are proline and dehydroproline, most preferred is proline.

Among the most preferred compounds of the present invention are:
D-Phe-Pro-Arg-CH$_2$Cl;
D-Tyr-Pro-Arg-CH$_2$Cl;
D-Phe-Dehydropro-ArgCH$_2$Cl;
D-Phe-Pro-Arg-CH$_2$Br;
wherein -ArgCH$_2$Cl represents:

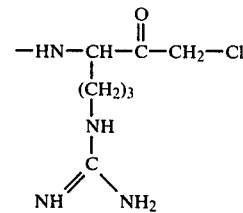
(8)

While the amino acid at position $P_3$ is always of the D-configuration, the amino acids at positions $P_1$ and $P_2$ are of the L-or natural configuration.

The peptide affinity label of the present invention can be prepared by the general methodology described in Kettner and Shaw in Biochemistry, Vol. 17, pp. 4778-4784 (1978). This paper, which is herein incorporated by reference, describes the generalized synthesis of peptides of arginine chloromethyl ketone. The following synthetic scheme represents an application, to the specific peptides of the present invention, of the methodology described in the aforementioned Kettner and Shaw reference.

Synthetic Scheme I:

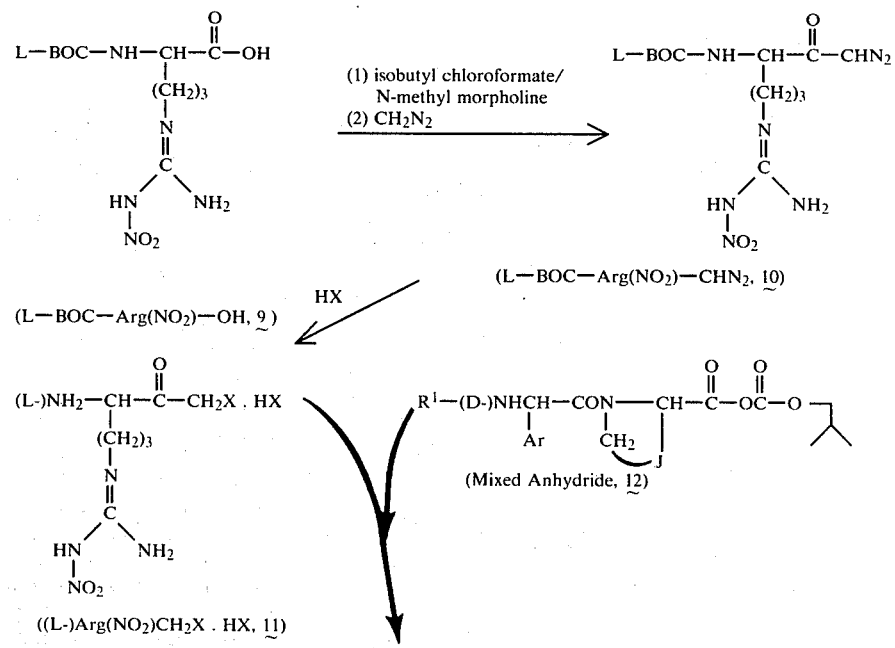

-continued

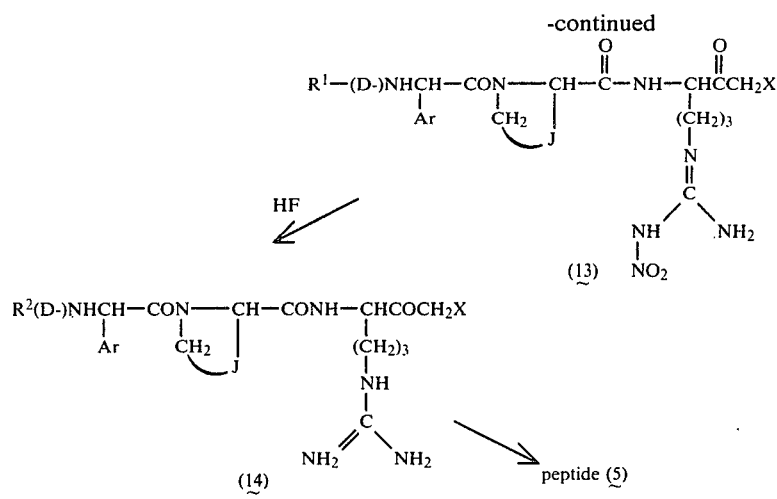

(13)

(14) peptide (5)

In this scheme, BOC stands for tert-butyloxycarbonyl, L- and D- stand for the L- or natural configuration and the D- or unnatural configuration of the amino acid α-carbons, X stands for a leaving group, preferably chlorine or bromine. Ar and J are defined above, $R^1$ is an acid labile amino protecting group, or a polypeptidyl residue blocked at its terminal amino group with an acid labile protecting group, $R^2$ stands for hydrogen or a polypeptidyl residue with a free terminal amino group.

BOC-L-Arg($NO_2$)-OH, the starting material, can be obtained commercially. In order to prepare the diazomethylketone of BOC-L-Arg($NO_2$)-OH, the starting material is reacted with isobutyl chloroformate in the presence of a base such as N-methyl morpholine to yield a mixed anhydride, which is then further reacted with ethereal diazomethane. BOC-L-Arg($NO_2$)-$CHN_2$ is thus obtained. This product is then dissolved in an inert, organic solvent and allowed to react with the conjugate acid of the leaving group X, such as for example, ethanolic hydrogen chloride, until nitrogen evolution ceases. In such case, the hydrogen halide salt of the resulting α-halomethyl ketone can then be isolated and purified in ether. The α-amino group of this α-halomethyl ketone is simultaneously deprotected by the hydrogen halide treatment and is thus free to react in the next step. L-Arg($NO_2$)$CH_2$X.HX is next coupled with the mixed anhydride 12, of the appropriate N-blocked amino acid, di- or polypeptidyl residue as shown in the scheme. The coupling reaction can normally be carried out in an inert solvent such as tetrahydrofuran in the presence of an amine such as triethylamine. Other appropriate solvents may be added when necessary to promote the solubility of starting materials or products. After evaporation of the solvent, extensive washing and drying, peptide 13 is obtained. Silica gel chromatography may be used at this stage to purify peptide 13. Peptide 13 contains a terminally protected amino group, and is either a tripeptide or a polypeptide ($R^1$=polypeptidyl residue). The guanidino function of the arginine residue at position $P_1$ is protected by a nitro group. Deprotection of the guanido group occurs next. Thus, treatment of peptide 13 with anhydrous HF at 0° C. in the presence of anisole yields peptide 14, containing the unprotected arginine residue at position $P_1$. In peptide 14, radical $R^2$ may be hydrogen, in which case peptide 14 is a tripeptide. $R^2$, on the other hand, may be a polypeptide residue containing a free terminal amino group. In both these cases, when the terminal amino group is free, peptide 14 corresponds, of course, to one of the final products of the invention. If it is desired to acylate the terminal amino group of the peptide, the same is treated appropriately with aroyl or acyl anhydride, or aroyl or acyl halide. It will be understood that when the mixed anhydride 12 is a polypeptide containing more than two amino acid residues, that any reactive amino acid residues (such as, for example, lysines, other arginines, carboxylic acids, etc.), may be protected and deprotected as necessary. Such protection and deprotection reactions are well known to those skilled in the art of polypeptide synthesis, as demonstrated by M. Bodanszky, Y. S. Klausner, and M. A. Ondetti "Peptide Synthesis (2nd Edition)", (G.A. Olah ed), 1976, John Wiley and Sons, N.Y.

Mixed anhydride 12 can be prepared from the free acid 13, by treatment with isobutylchloroformate/N-methyl morpholine:

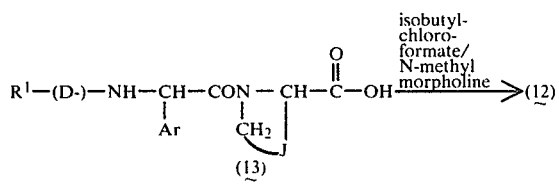

Free acid 13 is a polypeptide which may have 2–12 residues, with the proviso that the residue carrying the terminal carboxylate group is a cyclic derivative (residue $P_2$) and the next to the last residue ($P_3$) carries an aromatic amino acid of the D-configuration. Peptide 13 can be prepared by methods well known in the art of polypeptide synthesis; see e.g., Bodanszky et al, supra, and Considine, "Chemical and Process Technology Encyclopedia", pp 822–824. When synthesis is carried out in homogeneous phase, the peptide is obtained through the condensation of an amino acid or peptide containing a free carboxy group, and an amino acid or peptide containing a free amino group. A definite sequence can be constructed by repeating condensation with individual amino acid residues following the sequence by stepwise elongation or in some cases, by the condensation between two preformed peptide fragments. In such condensations, the amino and carboxy groups, which are not to participate in the reaction, must be blocked. Blocking groups should be readily introduced, stable to the condensation reaction and removed selectively from the accomplished peptide. Amino groups can be protected with a wide range of reagents. N-alkoxy carbonylation with benzyl or t-butyl chlorocarbonate is most widely used since the blocking group is readily decomposed by treating with HBr in glacial acetic acid. Other examples for amino blocking are tosylation, tritylation and phthaloylation or trifluoroacetylation. Carboxy groups are protected usually through formation of the ester. Once the peptide bond is formed, the ester linkage is hydrolized selectively in dilute alkaline solution at room temperature. A great range of reactive groups and side chains such as amino, carboxy, thio, hydroxy and so on, must be adequately blocked during peptide condensation reactions. The blocking must be stable to unmasking of the α amino or α-carboxy group for stepwise condensation and must be readily removed at the final stage. Formation of the peptide bond from amino and carboxy components is accomplished by activation of the carboxy components as acid halides anhydrides, azides or esters. Peptide synthesis has been automated by use of solid phase supports (Merrifield Synthesis). Thus, both homogeneous and heterogeneous synthetic procedures can be used to prepare the peptide 13 of the present invention.

The final products can be purified by various chromatographic procedures, such as silica gel, alumina gel, gel permeation, ion exchange, high pressure liquid chromatography, and the like.

The most preferred affinity label of the present invention is D-Phe-Pro-ArgCH$_2$Cl. This tripeptide affinity label is highly selective for thrombin and at a concentration of 10$^{-8}$ M inactivates the enzyme more than 95% in less than 3 minutes. A correlation between the inactivation of fibrinogen clotting activity and esterase activity exists for this tripeptide. D-Phe-Pro-ArgCH$_2$Cl is effective in preventing blood coagulation since, as mentioned previously, thrombin is the last protease in the cascade of protease-meidated reactions leading to the formation of blood clots. Increased concentrations of the halomethyl ketone tripeptide affinity label increases clotting times significantly.

Aside from the reactivity and selectivity of the peptide affinity label of the present invention for thrombin, the reagent reacts with other trypsinlike proteases at higher concentrations of reagent. Inactivation of these proteases is useful in many instances. Among them may be listed thrombocytin (Kirby et al, Biochem. 18, 3564 (1979)), crotalase, factor Xa, human plasma kallikrein, factor XIIa, plasmin, trypsin, complement protease C$_{1s}$, human urinary kallikrein, rat urinary kallikrein, the arginine specific protease from mouse submaxillary gland, and urokinase. The latter protease, urokinase, is a plasminogen activator of renal origin. Plasminogen activators from other sources should be readily inactivated by the peptides of this invention.

Since plasminogen activators have been detected in tumor growth, and since D-Phe-Pro-ArgCH$_2$Cl irreversibly inactivates plasminogen activators, the tripeptide affinity label as well as other peptides of the invention are potentially useful for the inhibition of tumor growth.

For example, D-Phe-ProArgCH$_2$Cl inactivates uterine plasminogen activator and plasminogen activator from a melanoma cell line.

Another use for the peptide affinity labels of the present invention is in the assay of proteolytic enzymes associated with hemostasis. Considerable effort has been devoted to the development of assays for these enzymes by the use of chromogenic substrates, but thrombin hydrolizes a number of these substrates (substrates for plasma kallikrein, factor Xa, and plasmin). Since D-Phe-Pro-Arg-CH$_2$Cl is a highly effective inactivator of thrombin, its use in conjunction with these substrates increases the selectivity of the assay.

When the affinity labels are used on animals, they may be administered by any means that promptly insures their interaction with thrombin and trypsin-like enzymes. Thus, the compounds of the present invention can be administered parenterally, subcutaneously, intravenously, intramuscularly, intraperitoneally, or by transfusion. The dosage administered will be dependent upon the age, health and weight of the recipient, kind of concurrent treatment, if any, frequency of treatment, and the nature of the effect desired. Generally, daily dosage of active ingredient compounds will be from about 0.05 mg to 100 mg per kg of body weight. Normally, from 1–30 mg per kg per day in one or more administrations per day is effective to obtain desired results. The compounds can be employed in dosage forms, such as tablets, capsules, powder packets or liquid solutions, suspensions or elixirs, if used for oral administration. Sterile liquid formulations such as solutions or suspensions can be prepared for parenteral use. In such compositions, the active ingredient will ordinarily always be present in an amount of at least 0.5% by weight based on the total weight of the composition and up to 99.9% by weight thereof.

Having now generally described this invention, the same will be better understood by reference to certain specific examples which are included herein for purposes of illustration only and are not intended to be limiting thereof.

CHEMICAL PREPARATIONS

EXAMPLE 1

Synthesis of D-Phe-Pro-Arg-CH$_2$Cl.2HCl.

BOC-L-Arg(NO$_2$)-OH(5.0 g, 15.6 mmoles) was dissolved in 60 ml of anhydrous tetrahydrofuran and was allowed to react with isobutylchloroformate (2.06 ml, 15.6 m moles) in the presence of N-methyl morpholine (1.72 ml, 15.6 m moles) for 4 hr. at $-20°$ C. The mixed anhydride preparation was filtered and the filtrate was added to 120 ml of etheral diazomethane. After stirring the reaction solution for 30 min. at 0° C., 80 ml of ether were added. The product crystallized from the reaction solution in the cold and was isolated by decanting the supernate and washing with ether. The diazomethylketone of BOC-L-Arg(NO$_2$)-OH was recrystallized from methanol to yield 2.57 g of product (mp 150° C.–151° C.).

Anal. calcd, for C$_{12}$H$_{21}$N$_7$O$_5$: C=41.97%, H=6.18%, and N=28.56%. Found: C=41.84%, H=6.27% and N=28.45%.

BOC-L-Arg(NO$_2$)—CHN$_2$ (1.47 g, 4.3 mmoles) was dissolved in a minimum volume of tetrahydrofuran and was allowed to react with ethanolic HCl (20 mmoles) at room temperature until nitrogen evolution ceased. Solvent was removed by evaporation and the residue was taken up in 40 ml of 1.8 N ethanolic HCl. After stirring the solution for 30 min. at room temperature, 1.34 g of an amorphous white solid were obtained by evaporating the solvent and triturating the residue with ether. The product was dried over KOH and P$_2$O$_5$ in vacuo and was used in subsequent reactions without further purification.

Benzoxycarbonyl-D-Phe-Pro-OH was prepared by saponofication of the corresponding methyl ester. The mixed anhydride of benzoxycarbonyl-D-Phe-Pro-OH (0.69 g, 17 mmoles) was prepared by reacting the acid with N-methyl morpholine (0.19 ml, 1.7 mmoles) and with isobutylchloroformate (0.23 ml, 1.7 mmoles) in 5 ml of tetrahydrofuran at $-20°$ C. for 10 minutes. Cold tetrahydrofuran, 20 ml containing triethylamine (0.24 m, 1.7 mmoles) was added and the mixture was immediately added to H-Arg($NO_2$)$CH_2$Cl.HCl (0.5 g, 1.7 mmoles) dissolved in 5 ml of cold N,N-dimethylformamide. The mixture was allowed to stir for 1 hr. at $-20°$ C. and 2 hrs. at room temperature. After adding 30 ml of tetrahydrofuran, the mixture was filtered and the filtrate was evaporated. The residue was dissolved in ethyl acetate and washed with a 0.2 M HCl, 5% $NaHCO_3$, and saturated aqueous sodium chloride. After drying over anhydrous sodium sulfate and evaporation, the product was purified by chromatography on a 2.5×60 cm column of 10–20$\mu$ silica gel. The column was eluted with chloroform: methanol (95:5) at a flow rate of 5.3 ml min$^{-1}$ and benzoxycarbonyl-D-Phe-Pro-Arg($NO_2$)$CH_2$Cl was eluted in the fraction from 59–71 min. After removing solvent by evaporation and triturating the product with ether, 0.57 g of benzoyxcarbonyl-D-Phe-Pro-Arg($NO_2$)$CH_2$Cl were obtained.

Anal. calcd. for $C_{29}H_{36}N_7O_7Cl$: C=55.27%, H=5.77% and N=15.56%. Found: C=55.15%, H=5.94% and N=15.31%.

Benzoxycarbonyl-D-Phe-Pro-Arg($NO_2$)$CH_2$Cl (0.52 g, 0.82 mmoles) was treated with approximately 15 ml of anhydrous HF for 40 min. at 0° C. in the presence of 1.0 ml anisole. After removing HF by distillation and drying over KOH in vacuo, the residue was dissolved in 10 ml of water and was extracted with 3×20 ml portions of ether. The aqueous phase was applied to a column containing 50 ml of SP-sephadex (C−25,H$^+$ form) and was washed with 150 ml of water. The product was eluted with 100 ml of 0.4 N HCl and the solution was lyophilized. The residue was triturated with ether to yield 0.4 g of product.

Thin layer chromatography on silica gel plates (Merck) with butanol:acetic acid:water (4:1:1) indicated a single spot, Rf 0.37, by uv and by ninhydrin and Sakaguchi stains. Amino acid analysis of the D-Phe-Pro-ArgCH$_2$Cl. 2HCl following hydrolysis in 2 ml of 6.0 N HCl for 24 hr. at 110° C. gave Phe=0.98 and Pro=1.00.

BIOLOGICAL TESTING IN VITRO

EXAMPLE 2

Reactivity of D-Phe-Pro-ArgCH$_2$Cl with Purified Thrombin

Figure 1:
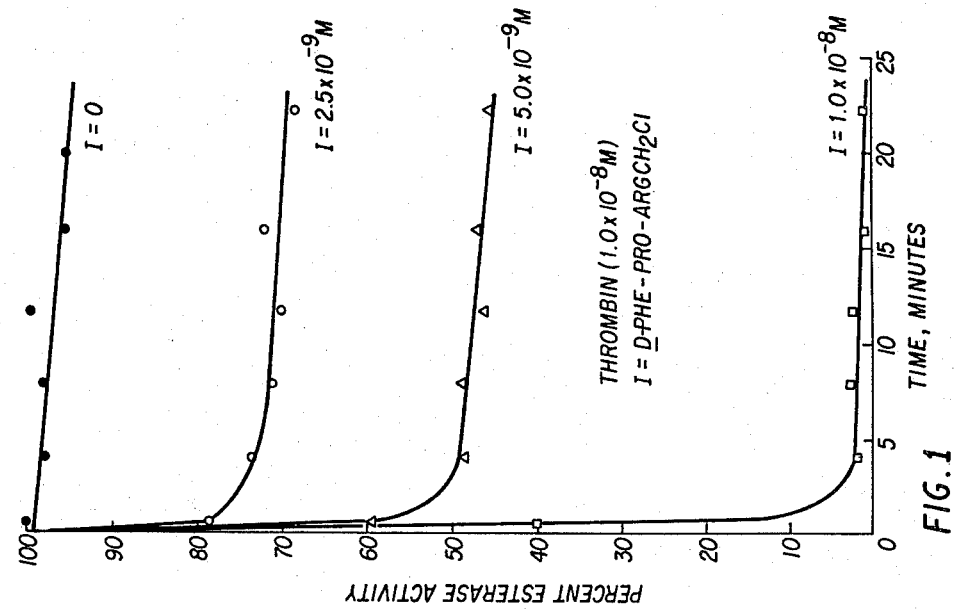
FIG. 1, describes the stoichiometry of inactivation of thrombin by D-Phe-Pro-Arg-CH$_2$Cl, according to Example 2.

The reactivity of thrombin with D-Phe-Pro-ArgCH$_2$Cl was determined by incubating the protease with the affinity label and determining the remaining esterase activity at timed intervals. The reaction was run in 50 mM Pipes buffer, pH 7.0, which was 0.20 M in NaCl at 25° C. 20 $\mu$l portions were removed at timed intervals and assayed for thioesterase activity (Kettner and Shaw, Biochemistry, 17, 4778 (1978)). As shown in FIG. 1, when $1.0 \times 10^{-8}$ M bovine thrombin was incubated with $1.0 \times 10^{-8}$ M D-Phe-Pro-ArgCH$_2$Cl, the esterase activity of the protease was inactivated by 97% in less than 5 min and no significant further change in activity was observed. The stoichiometry of the reaction was further established by incubating $1.0 \times 10^{-8}$ M thrombin with less than equal molar concentrations of D-Phe-Pro-ArgCH$_2$Cl, that is $5.0 \times 10^{-9}$ M and $2.5 \times 10^{-9}$ M. Thrombin was rapidly inactivated by even the higher dilution of affinity label and the degree of inactivation deviated by no more than 5% from that predicted for a complete reaction of thrombin with the available affinity label.

A correlation between the inactivation of fibrinogen clotting activity and esterase activity was established by reacting $4.5 \times 10^{-7}$ M thrombin with $2.25 \times 10^{-7}$ M D-Phe-Pro-ArgCH$_2$Cl under reaction conditions similar to those described for FIG. 1. The inactivation of bovine thrombin was found to be 51% by esterase assay and 48% by clotting assay; for human thrombin the values were 47% by esterase assay and 45% by clotting assay, (The theoretical value was 50%).

EXAMPLE 3

Selectivity of D-Phe-Pro-ArgCH$_2$Cl for Thrombin

The selectivity of D-Phe-Pro-ArgCH$_2$Cl for the inactivation of thrombin was determined by comparing its reactivity with thrombin with that of other plasma trypsin-like proteases such as plasmin, factor Xa and kallikrein. The proteases were incubated with D-Phe-Pro-ArgCH$_2$Cl in 50 mM Pipes buffer, pH 7.0; timed aliquots were removed and assayed for residual esterase activity. The initial concentrations of thrombin, plasma kallikrein, factor X$_a$, plasma and urokinase (not shown) were 0.23, 2.5, 14, 1.8 and 13 nM, respectively. As shown in FIG. 2, $5.0 \times 10^{-10}$ M D-Phe-Pro-ArgCH$_2$Cl inactivates $2.3 \times 10^{-10}$ M thrombin by 50% in less than 2 min. while other trypsin-like proteases were inactivated at least a 1,000 times less with D-Phe-Pro-ArgCH$_2$Cl (FIG. 2).

EXAMPLE 4

Anticoagulant Activity of D-Phe-Pro-ARgCH$_2$Cl

The high degree of reactivity of D-Phe-Pro-ArgCH$_2$Cl with thrombin indicates that it should be effective in blocking blood coagulation since thrombin is the last protease in the cascade of protease mediated reactions leading to the formation of blood clots. The effect of D-Phe-Pro-ArgCH$_2$Cl on clotting was determined by measuring its effect on thromboplastin times and the partial thromboplastin times of citrated human plasma. As shown in Tables I and II, 0.50–0.10 $\mu$M D-Phe-Pro-ArgCH$_2$Cl increases the partial thromboplastin time (inhibits clotting) by 50% and at 0.1 to 0.5 $\mu$M increases the prothrombin time by 50% while at higher levels clotting is progressively inhibited.

TABLE I

The Effect of D-Phe—Pro—ArgCH$_2$Cl on the Partial Thromboplasin Times of Human Plasma[a]

| Concentration of Affinity label (M) | Clotting Times (Sec) |
| --- | --- |
| 0 | 47.8 ± 0.3 |
| 5.0 × 10$^{-9}$ | 53.0 ± 1.4 |
| 1.0 × 10$^{-8}$ | 54.8 ± 1.1 |
| 5.0 × 10$^{-8}$ | 69.8 ± 3.2 |
| 1.0 × 10$^{-7}$ | 81.6 ± 1.2 |
| 5.0 × 10$^{-7}$ | 149.2 ± 0.9 |

TABLE I-continued

The Effect of D-Phe—Pro—ArgCH$_2$Cl on the Partial Thromboplasin Times of Human Plasma[a]

| Concentration of Affinity label (M) | Clotting Times (Sec) |
|---|---|
| $7.5 \times 10^{-7}$ | $180.7 \pm 4.9$ |

[a]Plasma (0.100 ml) was activated by incubation for 6 min. with 0.100 ml of a suspension consisting of rabbit brain cephalin and 2% Kaolin in 0.9% NaCl at 37° C. Clotting was initiated by adding 0.100 ml of 0.20 M CaCl$_2$. D-Phe—Pro—ArgCH$_2$Cl was introduced with the CaCl$_2$.

TABLE II

Effect of D-Phe—Pro—ArgCH$_2$Cl on the Prothrombin Times of Human Plasma[a]

| Concentration of Affinity Label (M) | Clotting Times (Sec) |
|---|---|
| 0 | $13.2 \pm 0.2$ |
| $1.0 \times 10^{-8}$ | $14.1 \pm 0.1$ |
| $5.0 \times 10^{-8}$ | $15.1 \pm 0.05$ |
| $1.0 \times 10^{-7}$ | $15.6 \pm 0.3$ |
| $5.0 \times 10^{-7}$ | $24.3 \pm 0.3$ |

[a]Plasma (0.100 ml) was incubated with the inhibitor at 37° C. Clotting was initiated by adding 0.200 ml of General Diagnostic's simplastin (commercial preparation of CaCl$_2$ and tissue thrombo-plastin) (Singer, J.W. and Sibley, C.A.; Am. J. Clin. Pathol., 59, 755-759 (1973); Kleiner, E.E., Heiges, L., and Fukushima, M.; Am. J. Clin. Pathol., 56, 162-165 (1971)) and clotting times were noted.

COMPARATIVE EXAMPLES

Table III, infra, shows the relative effectiveness of various chloromethyl ketones of the prior art in the inactivation of thrombin at 25° C., pH 7.0, with a tripeptide of the present invention, D-Phe-Pro-ArgCH$_2$Cl.

The values of $k_{app}/I$ were obtained from Kettner and Shaw, "The Chemistry and Biology of Thrombin", supra.

Structure/function relationships of proteases and affinity labels are usually evaluated by measuring the apparent, pseudo-first-order rate constant $k_{app}$, observed for the inactivation of the protease on incubation with the affinity label in a large molar excess. Under these conditions, the dissociation constant $K_i$, (see Equations 1 and 2), for the reversible complex and the rate constant for the alkylation step of the affinity labeling reaction, $k_2$, can be evaluated for the affinity labeling mechanism of Equation 4, supra. For comparison of the reactivity of different affinty labels with a protease, the second order rate constant, $k_2/K_i$, can be established using the relationship in Equation 15:

$$k_{app}/I = k_2/K_i \text{ if } I \ll K_i \quad (15)$$

where I is the concentration of the affinity label.

The high reactivity of thrombin with D-Phe-Pro-ArgCH$_2$Cl imposed a limitation on achieving the conditions of Equation 15, since dilution of thrombin to obtain pseudo-first-order reaction conditions were beyond the sensitivity of the esterase assay using thiobenzyl benzyloxy carbonyl-L-lysinate (Green, G. D. J. and Shaw, E. (1979) Anal. Biochem., 93, 223-226), one of the most sensitive assays for trypsin-like proteases. It is possible however, to obtain an estimate of the rate of inactivation of $2.3 \times 10^{-10}$ M human thrombin by $5.0 \times 10^{-10}$ M D-Phe-Pro-ArgCH$_2$Cl. From FIG. 2, this level of affinity label inactivates the proteolytic enzyme by 50% in less than 2 minutes. A value of $k_{app}/I$ of $6.9 \times 10^8$ M$^{-1}$ min$^{-1}$ can be calculated for the inactivation of thrombin, assuming that the half-life for inactivation is 2 minutes. It should be noted that this value is probably a conservative estimate of the second order rate constant, $k_2/K_i$, since the relationship of Equation 15 is valid for other affinity labels of thrombin only at slower rates of inactivation.

TABLE III

Relative Effectiveness of Chloromethyl Ketones in the Inactivation of Thrombin

| | Conc. of inhibitor (M) | $t_{\frac{1}{2}}$[a] (min) | $k_{app}/[I]$[b] (min$^{-1}$M$^{-1}$) $\times 10^{-4}$ | Ref |
|---|---|---|---|---|
| (1) Val-Pro-ArgCH$_2$Cl | $7.5 \times 10^{-8}$ | 17 | 54.00 | (c) |
| (2) Pro-Phe-ArgCH$_2$Cl | $5.0 \times 10^{-5}$ | 35 | 0.04 | (c) |
| (3) Pro-Gly-ArgCH$_2$Cl | $1.0 \times 10^{-6}$ | 57 | 1.20 | (c) |
| (4) Glu-Gly-ArgCH$_2$Cl | $1.0 \times 10^{-6}$ | 31 | 2.20 | (c) |
| (5) Val-Val-ArgCH$_2$Cl | $1.0 \times 10^{-6}$ | 33 | 2.10 | (c) |
| (6) Gly-Val-ArgCH$_2$Cl | $2.0 \times 10^{-6}$ | 18 | 1.90 | (c) |
| (7) Ile-Pro-ArgCH$_2$Cl | $7.5 \times 10^{-8}$ | 22 | 42.00 | (c) |
| (8) Val-Ile-Pro-ArgCH$_2$Cl | $7.5 \times 10^{-8}$ | 13 | 73.00 | (c) |
| (9) D-Phe-Pro—ArgCH$_2$Cl | $5.0 \times 10^{-10}$ | <2 | 69,000 | |

[a]$t_{\frac{1}{2}}$ is the half time for the pseudo-first-order inactivation of thrombin at 7.0 and 25° C.
[b]$k_{app}/[I]$ is the ratio of the apparent, first order rate constant for inactivation of thrombin to the concentration of affinity label.
[c]Kettner and Shaw, "Chemistry and Biology of Thrombin", Ann Arbor Science Publishers, Inc., pp 129-143 (1977).

The data in Table III indicates that D-Phe-Pro-ArgCH$_2$Cl is, conservatively, more than 1,000 times better as an affinity label than the best prior art tripeptide affinity label, Val-Pro-ArgCH$_2$Cl. It is between 10$^4$ and 10$^5$ times better than the average prior art tripeptide affinity label. Of particular interest is the observation that the placement of a D-Phe residue in the P$_3$ position improves the inactivation rate by approximately three orders of magnitude when compared to tripeptides 1 and 7, which have L-Val and L-Ile P$_3$ residues, respectively. These two prior art tripeptides are otherwise identical to the tripeptide of the invention in their P$_1$ and P$_2$ residues.

Bajusz et al (Peptides: Chemistry, Structure, Biology, supra) have shown that the aldehyde D-Phe-Pro-Arg-H is a highly effective reversible inhibitor of thrombin. The K$_i$ is $7.5 \times 10^{-8}$ (Bajusz et al, supra, page 603, last line). The effectiveness of chloromethyl ketones as irreversible affinity labels for thrombin has been shown to correspond to the affinity of thrombin for the chloromethyl ketone (Kettner and Shaw in "Chemistry and Biology of Thrombin", supra). In other words, the effectiveness is inversely proportional to the magnitude K$_i$; the more effective affinity labels having smaller dissociation constants K$_i$.

This is demonstrated in Table IV which compares the kinetic constants for four prior art tripeptide affinity labels, for an affinity label according to the present invention, D-Phe-Pro-ArgCH$_2$Cl, and K$_i$ for the aldehyde D-Phe-Pro-Arg-H.

TABLE IV

Comparison of Kinetic Constants

| Inhibitor | K$_i$ (M) | k$_2$ (min$^{-1}$) | k$_2$/K$_i$ (min$^{-1}$M$^{-1}$) | Ref |
|---|---|---|---|---|
| Phe-Ala-LysCH$_2$Cl | $3.7 \times 10^{-5}$ | 0.34 | $0.09 \times 10^5$ | (a) |
| Gly-Val-ArgCH$_2$Cl | $1.3 \times 10^{-5}$ | 0.30 | $0.23 \times 10^5$ | (a) |
| Phe-Ala-ArgCH$_2$Cl | $2.9 \times 10^{-6}$ | 0.26 | $0.90 \times 10^5$ | (a) |
| Val-Pro-ArgCH$_2$Cl | $6.7 \times 10^{-7}$ | 0.31 | $4.00 \times 10^5$ | (a) |
| D-Phe-Pro-Arg-H | $7.5 \times 10^{-8}$ | — | — | (b) |
| D-Phe-Pro-ArgCH$_2$Cl | — | — | $6900 \times 10^5$ | (c) |

(a) See Table III, reference (c).
(b) Bajusz et al, supra.
(c) k$_2$/K$_i$ ≈ k$_{app}$/I from Table III.

The data in Table IV shows that the effectiveness of inactivation, given by the ratio k$_2$/K$_i$ increases from $0.09 \times 10^5$ to $4.00 \times 10^5$ when the value of K$_i$ decreases from $3.7 \times 10^{-5}$ to $6.7 \times 10^{-7}$. From the K$_i$ value of $7.5 \times 10^{-8}$ for the aldehyde D-Phe-Pro-Arg-H, and assuming approximately the same value of K$_i$ for the affinity label D-Phe-Pro-ArgCH$_2$Cl, one would have predicted a k$_2$/K$_i$ ratio for D-Phe-Pro-ArgCH$_2$Cl in the range of (40–200)$\times 10^5$. The k$_2$/K$_i$ ratio for the affinity label however, is $6900 \times 10^5$, a value which is between 30 and 150 times larger than that predicted. This difference of between 1 and 2 orders of magnitude can therefore be attributed to an unexpected increase in the first order rate constant of covalent inactivation, k$_2$, or to the greater affinity of thrombin for the arginyl chloromethyl ketone than for the arginyl aldehyde.

BIOLOGICAL STUDIES IN VIVO

D-Phe-Pro-ArgCH$_2$Cl blocks thrombosis in rabbits. Intravenous injection of 1 mg of inhibitor followed by intravenous infussion of 1,200 NIH units of thrombin (or 250 μg) over a period of 5 min. had no effect on the animal. On the other hand, infusion of thrombin without administering inhibitor resulted in death of the animal due to massive thrombosis before the end of the 5 min. infussion. This level of inhibitor is a 100-1000 times greater than the LD$_{50}$ of the reagent in mice.

What is claimed as new and intended to be secured by Letters Patent of the United States is:

1. A peptide affinity label of the formula:

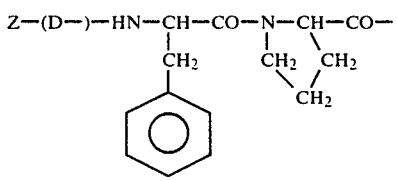

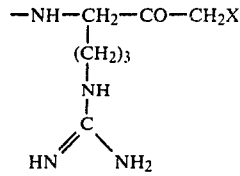

or a hydrohalic acid addition product thereof; wherein X is a halogen atom, and Z is hydrogen or C$_1$-C$_6$ acyl.

2. The peptide of claim 1 wherein X is chlorine or bromine.

3. The peptide of claim 1 wherein Z is hydrogen.

4. The peptide of claim 1 which is:

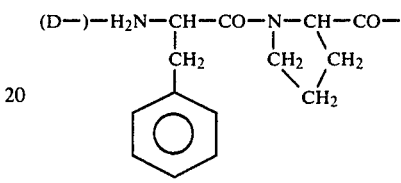

5. A compound of the formula:

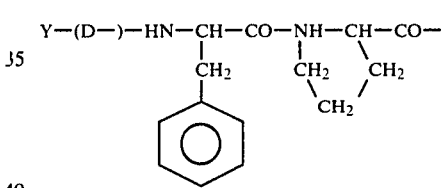

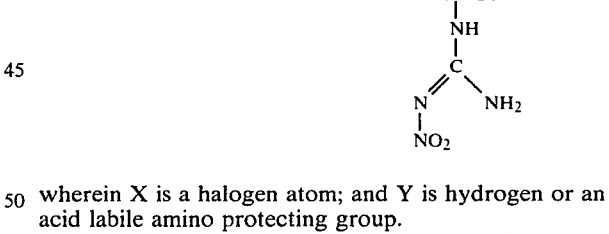

wherein X is a halogen atom; and Y is hydrogen or an acid labile amino protecting group.

6. The compound of claim 5 wherein X is chlorine or bromine.

7. The compound of claim 5 wherein X is chlorine.

8. The compound of claim 5 wherein Y is an acid labile amino protecting group selected from the group consisting of benzyloxy carbonyl, t-butyloxycarbonyl tosyl, trityl, phthaloyl and trifluoroacetyl.

9. The compound of claim 8 wherein Y is benzyloxycarbonyl or t-butyloxycarbonyl.

10. An anticoagulant composition which comprises anticoagulating effective amounts of a peptide from claim 1 together with a pharmacologically inert carrier.

11. The composition of claim 10, wherein the peptide is D-Phe-Pro-ArgCH$_2$Cl.

12. A method of irreversibly inhibiting thrombin which comprises reacting said thrombin with the affinity label of claim 1.

* * * * *

UNITED STATES PATENT AND TRADEMARK OFFICE
CERTIFICATE OF CORRECTION

PATENT NO. : 4,318,904

DATED : March 9, 1982

INVENTOR(S) : ELLIOTT N. SHAW ET AL

It is certified that error appears in the above—identified patent and that said Letters Patent is hereby corrected as shown below:

In the Abstract--Line 4, after the formula, delete "A" and substitute therefor --Ar--.

Column 9, line 21--after "halides" insert --,-- (comma).

Column 9, line 40--delete "protease-meidated" and substitute therefore --protease-mediated--.

Column 13, line 66--delete "affinty" and substitute therefor --affinity--.

Column 2, line 45--delete "Nüis" and substitute therefor --Nü is--.

Column 3, line 6--delete "a".

Column 3, line 39--delete "where" and substitute therefor --wherein--.

Column 4, line 68--delete "BlombULM/a/ck" and substitute therefor --Blombäck--.

Column 11, line 4--delete "saponofication" and substitute therefor --saponification--.

Column 12, line 41--delete "ARgCH$_2$Cl" and substitute therefor --ArgCH$_2$Cl--.

UNITED STATES PATENT AND TRADEMARK OFFICE
CERTIFICATE OF CORRECTION

PATENT NO. : 4,318,904

DATED : March 9, 1982

INVENTOR(S) : ELLIOTT N. SHAW ET AL

It is certified that error appears in the above—identified patent and that said Letters Patent is hereby corrected as shown below:

Column 14, Table III--line (9) should read as follows:

| | Conc. of inhibitor (M) | $t_{\frac{1}{2}}^{(a)}$ (min) | $k_{app}/[I]^{(b)}$ $(min^{-1}M^{-1}) \times 10^{-4}$ | Ref |
|---|---|---|---|---|
| (9) D-Phe-Pro-ArgCH$_2$Cl | 5.0 x 10$^{-10}$ | <2 | 69,000 | |

Signed and Sealed this

Thirteenth Day of July 1982

[SEAL]

Attest:

Attesting Officer

GERALD J. MOSSINGHOFF

Commissioner of Patents and Trademarks